United States Patent [19]
Fan et al.

[11] Patent Number: 5,223,220
[45] Date of Patent: Jun. 29, 1993

[54] SOLID PHASE IMMUNOASSAY DEVICE AND METHOD OF MAKING SAME

[75] Inventors: Eugene Fan, La Jolla; Sinfu Tzeng, San Francisco; Fon-Chiu M. Chen, Ramona; Ching Huang, Chula Vista; Dou-Mei Wang, Encinitas; Theresa Popejoy, Poway, all of Calif.

[73] Assignee: Pacific Biotech, Inc., San Diego, Calif.

[21] Appl. No.: 917,800

[22] Filed: Jul. 20, 1992

Related U.S. Application Data

[63] Continuation of Ser. No. 500,005, Mar. 27, 1990, abandoned.

[51] Int. Cl.$^5$ ............... G01N 21/00; B65D 77/20
[52] U.S. Cl. ............... 422/58; 422/56; 422/57; 422/101; 206/216; 206/564; 206/570; 435/805; 436/169
[58] Field of Search ............... 422/56-58, 422/101; 435/293, 300, 301, 805; 436/167, 169; 206/216, 564, 570

[56] References Cited

U.S. PATENT DOCUMENTS

| | | | |
|---|---|---|---|
| 3,343,897 | 9/1967 | Keller | 206/216 X |
| 3,981,398 | 9/1976 | Boshoff | 206/570 |
| 3,990,852 | 11/1976 | Piazzi et al. | 435/301 X |
| 4,017,261 | 4/1977 | Svoboda et al. | 436/66 X |
| 4,169,138 | 9/1979 | Jonsson | 422/57 |
| 4,373,932 | 2/1983 | Gribnau et al. | 436/501 |
| 4,376,110 | 3/1983 | David et al. | 435/5 |
| 4,496,654 | 1/1985 | Katz et al. | 422/56 |
| 4,518,565 | 5/1985 | Boger et al. | 435/805 X |
| 4,552,839 | 11/1985 | Gould et al. | 422/56 |
| 4,591,570 | 5/1986 | Chang | 435/7.24 |
| 4,632,901 | 12/1986 | Valkirs et al. | 422/56 |
| 4,703,017 | 10/1987 | Campbell et al. | 436/501 |
| 4,774,192 | 9/1989 | Terminiello et al. | 422/56 X |
| 4,855,240 | 8/1989 | Rosenstein et al. | 422/56 |
| 4,857,453 | 8/1989 | Ullman et al. | 422/58 X |
| 4,912,034 | 3/1990 | Kalra et al. | 422/56 |
| 4,943,522 | 7/1990 | Eisinger et al. | 422/57 X |
| 4,960,691 | 10/1990 | Gordon et al. | 422/58 X |
| 4,981,786 | 1/1991 | Dafforn et al. | 422/56 X |
| 5,006,474 | 4/1991 | Horstman et al. | 422/58 X |
| 5,147,609 | 9/1992 | Grenner | 422/56 X |

FOREIGN PATENT DOCUMENTS

| | | |
|---|---|---|
| 0323605 | 12/1988 | European Pat. Off. |
| 8001515 | 1/1980 | PCT Int'l Appl. |
| 8808534 | 4/1988 | PCT Int'l Appl. |
| 2204398 | 4/1988 | United Kingdom |

Primary Examiner—James C. Housel
Assistant Examiner—Arlen Soderquist
Attorney, Agent, or Firm—Knobbe, Martens, Olson & Bear

[57] ABSTRACT

In response to an express need for an immunoassay device with universal applicability, which further promotes the goals of inventory reduction and simplified, less costly manufacture, a container for holding materials used in conjunction with an immunoassay, having a housing with an inside, an outside, and a top, wherein the top is provided with a plurality of apertures communicating with the inside of the housing, and a thin web of opaque material applied over the top of the housing covering at least one but not all of the apertures.

12 Claims, 2 Drawing Sheets

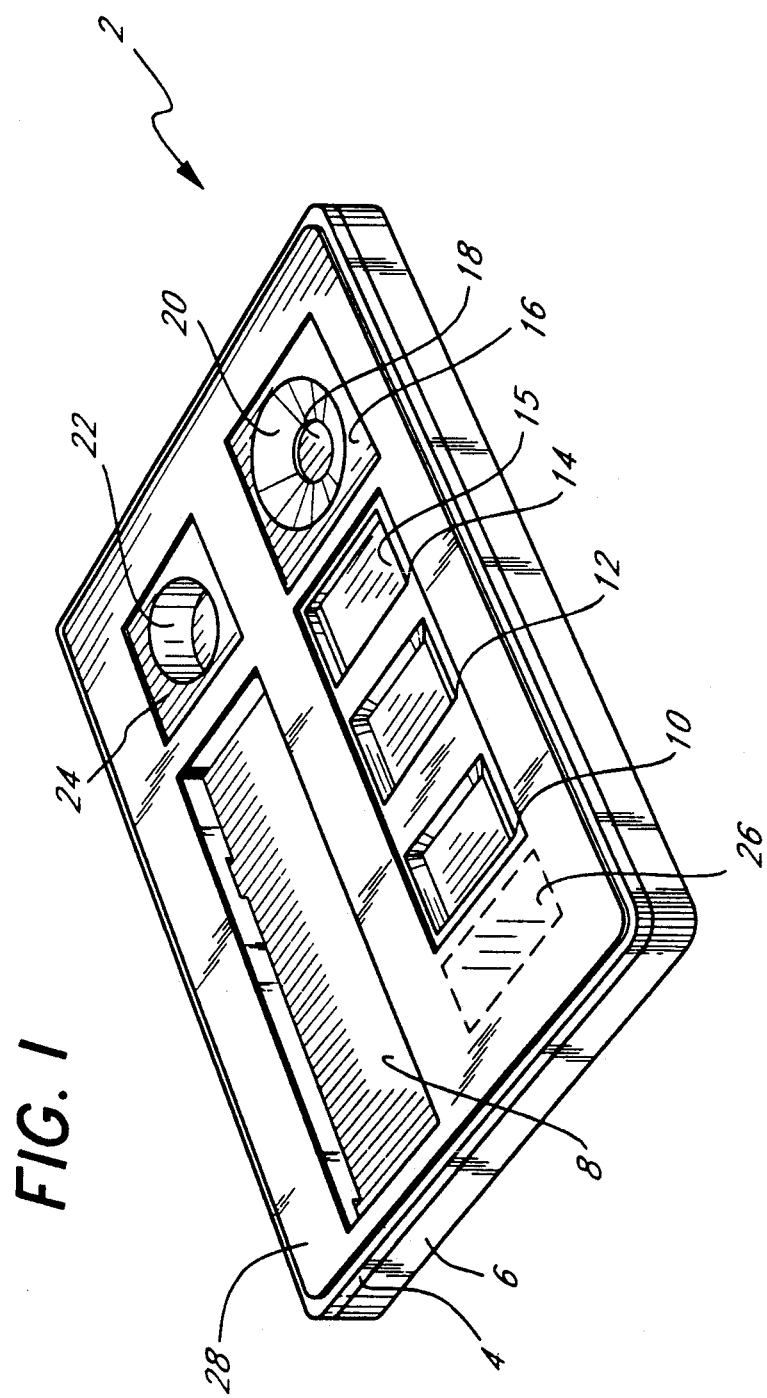

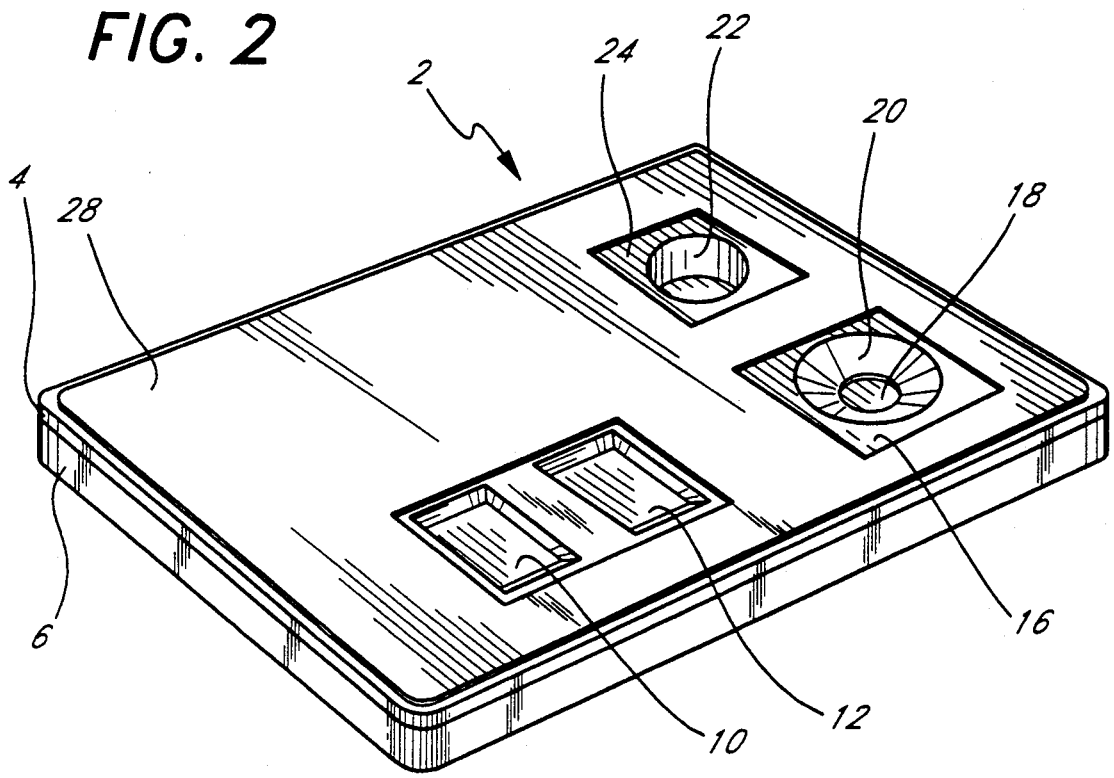
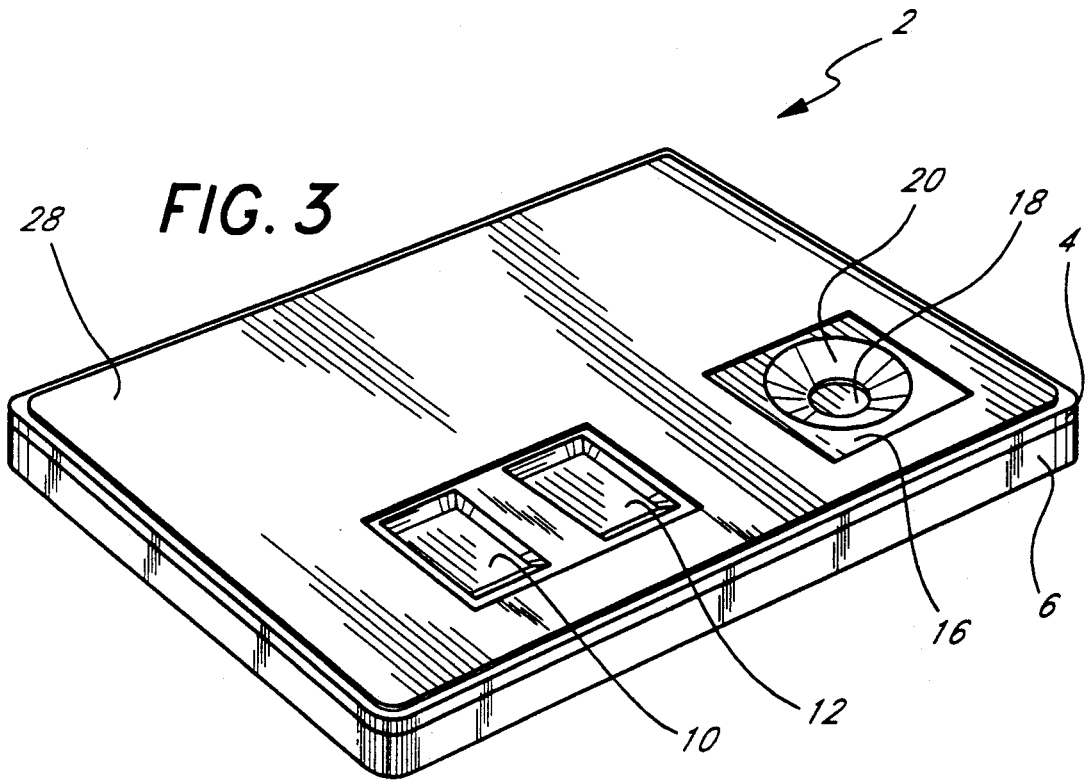

SOLID PHASE IMMUNOASSAY DEVICE AND METHOD OF MAKING SAME

This application is a continuation of application Ser. No. 07/500,005, filed Mar. 27, 1990, now abandoned.

BACKGROUND OF THE INVENTION

A number of devices of varying design formats presently coexist on the market. In addition to devices requiring a multiplicity of tubes, vials and support structures, there are now various immunoassay devices encased in rigid containers or cases of varying designs, shapes and colors. For the individual manufacturer who produces a variety of devices, variations in container formats increase production costs, largely because there is no uniformity of manufacturing or assembly techniques, components differ, and labeling of each type of device must necessarily change as well.

Therefore, in response to an express need for an immunoassay device with universal applicability, which further promotes the goals of inventory reduction and simplified, less costly manufacture, the Applicants hereby disclose the present invention, including equivalents thereof.

SUMMARY OF THE INVENTION

According to one aspect of the present invention, there is provided a container for holding materials used in conjunction with an immunoassay, comprising a housing having an inside, an outside, and a top, wherein the top is provided with a plurality of apertures communicating with the inside of the housing, and a thin web of opaque material applied over the top of the housing covering at least one but not all of the apertures. In a preferred embodiment, the container further comprises wicking material inside the housing extending between at least two of the apertures, wherein a first aperture is adapted to receive a sample and deposit it on a first portion of the wicking material, and a second the aperture is adapted to permit viewing of the results of a completed assay on a second portion of the wicking material.

In yet another embodiment, the wicking material also extends to a third aperture, which aperture is adapted to permit application of reagents to the wicking material before application of the thin web to the housing, which third aperture is covered by the thin web. In another preferred embodiment, the wicking material also extends to a fourth aperture, the fourth aperture adapted to permit viewing of a signal on the wicking material indicative of completion of the assay. In another variation, the wicking material is in fluid flow contact with an absorbent material adjacent to the fourth aperture.

In another variation of the invention, the top of the housing further has a well formed therein for holding a container for liquid used in the assay. In another embodiment, the top of the container further has an opening therein for receiving a desiccant material, which opening is covered by the thin web. In a particularly preferred embodiment, the thin web comprises paper or plastic.

Another embodiment of the present invention is an immunoassay device, comprising a housing having an inside, an outside, and a top, wherein the top is provided with a plurality of apertures communicating with the inside of the housing, wicking material inside the housing, reagents used in the assay located on the wicking material, and an absorbent material in fluid contact with the wicking material, in such manner that reverse flow of tracer, label, specimen or specimen components back onto the wicking material is prevented. A thin web of opaque material may also be applied over the top of the housing.

Yet another embodiment of the present invention is an immunoassay device, comprising a housing having an inside, an outside, and a top, wherein the top is provided with a plurality of apertures communicating with the inside of the housing, and wicking material inside the housing extending between at least three of the apertures (wherein a first such aperture is adapted to receive a sample and deposit it on a first portion of the wicking material, a second such aperture is adapted to permit viewing of the results of a completed assay on a second portion of the wicking material, and a third such aperture is located between the first and second apertures), reagents used in the assay located on the wicking material beneath the third aperture, a well formed in the housing adapted to hold a container of liquid used in the assay, and a thin web of opaque material applied over the top of the housing covering one or more of the well and the third aperture.

In another embodiment, the device further contains a desiccant material in the housing with an opening provided in the top of the housing over the desiccant, wherein the thin web covers the opening. In yet another embodiment, an absorbent material is in fluid contact with the wicking material, in such manner that sample is applied to the absorbent material at the first aperture prior to contacting the wicking material. In another variation, the device contains an absorbent material in fluid contact with the wicking material, in such manner that reverse flow of tracer or label, such as colored particles (e.g., latex), back onto the wicking material is prevented. In yet another embodiment, the absorbent material further prevents the reverse flow of sample or sample components back onto the wicking material.

Another preferred embodiment discloses a method for constructing immunoassay devices, particularly those of the present invention, comprising the steps of providing a housing having an inside, an outside, and a top having a plurality of apertures communicating with the inside of the housing, inserting a web of wicking material inside the housing extending between first, second, and third the apertures, so that the web is accessible through the first, second, and third apertures and the third aperture is located between the first and second apertures, applying a first reagent to the web through the second aperture, which first reagent is bound to the web, applying a second reagent to the web through the third aperture, which second reagent is mobile when liquid is added to the first aperture, and is adapted to cooperate with an analyte in a sample and the first reagent to create a signal indicative of the results of the assay, which signal can be read through the third window, and thereafter applying a thin web of opaque material over the top of the housing over the third aperture but not over the first and second apertures, to form a first immunoassay device. The method for constructing immunoassay devices may further comprise the step of inserting an absorbent material into the housing before applying the top of the housing.

The method for constructing immunoassay devices may utilize a device wherein the top of the housing has an opening therethrough for receiving a desiccant, and may further comprise the steps of inserting a desiccant into the housing through the opening before applying the thin web, and applying the thin web over the opening.

Yet another embodiment of the method for constructing immunoassay devices includes the step of repeating the aforementioned steps, except that in the step of applying the thin web, at least one aperture that was covered by the thin web in the first immunoassay is not covered, to form a second immunoassay device for performing an immunoassay different from that adapted to be performed by the first immunoassay device.

BRIEF DESCRIPTION OF THE DRAWINGS

FIG. 1 is a perspective view of a preferred embodiment of the device of the present invention.

FIG. 2 is a perspective view of the device of the present invention having an opaque label covering some of the openings shown in FIG. 1.

FIG. 3 is a perspective view of the device of the present invention having an opaque label covering other of the openings shown in FIG. 1.

DETAILED DESCRIPTION

Referring to FIG. 1, there is shown an immunoassay device 2, which is generally comprised of an upper "card" member 4 and lower "card" member 6. The upper and lower card members 4, 6 are adapted to mate together to form a housing. The upper card member 4 may be provided with at least six apertures, including a tracer loading port 14, sample loading port 16, and test view ports 10 and 12. In addition, the upper card member 4 is provided with a sample container/cup holding port 22 and an elongated aperture 8 into which a desiccant material may be placed. A wicking material 15, preferably nitrocellulose, is placed between the upper and lower card members 4 and 6, respectively, and it extends underneath ports 10, 12, 14 and 16 with a portion of wicking material 15 being visible through ports 10, 12, and 14. The wicking material 15 is thus held in place between card members 4 and 6. At least a portion of wicking material 15 which is viewable through port 12 includes a binder specific for the analyte to be assayed and defines a test area. A first absorbent material, preferably in the form of an absorbent pad 18, is also placed between upper and lower card members 4 and 6, respectively, in such a manner that absorbent pad 18 is visible through port 16. Pad 18 is preferably in fluid or flow contact with wicking material 15. An indicator material or signal-producing substance may be applied to wicking material 15 viewable through port 10, to provide a signal indicating the completion of the assay or indicating a result. A second absorbent pad or "end" pad 26, shown in phantom lines on FIG. 1, is also placed between upper and lower card members 4 and 6 respectively, in such a manner that, albeit it may not be observable from the outside of the device 2, it is in fluid or flow contact with wicking material 15, preferably at the opposite end of wicking material 15 from first absorbent pad 18.

As particularly shown, the sample loading port 16 is closer to the tracer loading port 14 than the viewing windows, whereby the capillary flow path between ports 16 and 14 is shorter than the capillary flow path between ports 16 and 12.

In an assay, a sample to be assayed is applied through test port 16, a binder has been applied at port 12, and tracer has been applied through port 14. The sample flows along the wicking material 15 and contacts tracer at port 14. The sample then flows further along the wicking material 15 to test ports 12 and 10 respectively. As hereinabove indicated, the flow path of the wicking material is set up in a manner such that the sample contacts the tracer on the wicking material 15 prior to contact of the sample with the binder at port 12. The binding of tracer may then be determined through test port 12. The presence and/or amount of analyte present in the sample may be determined by the presence and/or amount of tracer as determined through port 12 of the device 2. In addition, if an indicator substance has been applied through test port 10, the completion of the assay may be determined. As shown in FIGS. 1-3, a thin web of opaque material 28 may also be applied over the top of the device 2 to cover various openings so that different assay formats can be provided using the same basic device 2 with different opaque webs 28. Thus, as illustrated in FIG. 2, an assay can be provided using the same upper and lower card members 4, 6 shown in FIG. 1, except that the tracer loading port 14 and the aperture 8 have been covered by the opaque material 28. FIG. 3 corresponds to FIG. 2, except that the sample cup holding port 22 has also been covered by the opaque material 28.

In accordance with the preferred embodiment, as hereinabove described, by using an appropriate material as wicking material 15 (for example, nitrocellulose) and a tracer which may include a visible particulate label (such, as colored latex), it is possible to determine binding of tracer through port 12 without destruction of the label.

Although the embodiment has been described with respect to the use of a tracer which includes a visible particulate label, it is to be understood that other detectable labels may be employed within the spirit and scope of the invention. For example, labels such as enzyme labels, chromogen labels, fluorescent and/or absorbing dyes may be used. In such cases, it may be necessary to add an additional substance in order to detect the label in port 12; for example, in the case of an enzyme label, a substrate may be added to produce detectible color in port 12. It is also possible to provide a second test port 10 to signal the end of the assay. In this manner, tracer which has not been bound in wicking material portion 12 may be determined. The presence and/or amount of tracer visible in port 12 may be employed to determine analyte alone and/or in conjunction with the presence and/or amount of analyte visible in port 10.

The invention can be better understood by way of the following examples which are representative of the preferred embodiments thereof, but which are not to be construed as limiting the scope of the invention.

EXAMPLE I

A reaction unit 2 was constructed using two plastic "card" members 4 and 6. The cards were made of polystyrene. Upper card 4 has a thickness of approximately 1 mm. Lower card 6 has a thickness of approximately 1 mm and has walls extending perpendicularly upward on all four sides, said walls joined at their corners, with said corners preferably being rounded, as illustrated in FIG. 1. When top card member 4 and bottom card member 6 are joined together, the unit has an apparent "thickness" of about 6 mm. The top card member 4 has six apertures which include an elongated port 8, tracer loading port 14, sample loading port 16, sample cup holding port 22, wicking material visible under ports 10, 12, and 14, and test ports 10 and 12. Ports 10, 12 and 14 have dimensions of approximately 10 mm×10 mm., while application port 16 has a diameter of about 7 mm. Aperture 8 has a dimension of about 20 mm×50 mm, while aperture 22 has a diameter of about 13 mm.

Sample loading port 16 has shallow, sloping sides 20, which slope downward toward a circular aperture in which an absorbent material or pad 18, which is connected to the wicking material 15, is located. In a preferred embodiment, pad 18 is located underneath a portion of wicking material 15. A filtering device (not shown) may also be placed atop the sample loading port 16 to filter out particulates or other materials that may be in a sample to be applied. In another embodiment, additional absorbent material, in the form of pad 26, may be placed in fluid contact with wicking material 15 adjacent to port 10, for example, to absorb additional fluids once the sample has been wicked past port 10.

First absorbent pad 18 visible through port 16 receives the sample and releases it to the wicking material 15. Pad 18 may comprise, for example, a compact cellulose material such as D28, 17 Chr. (Whatman Manufacturing Inc., N.J.), a more porous material such as GF/A or GF/D (Whatman Manufacturing Inc., N.J.), or extra thick glass fiber filter (such as that available from Gelman Sciences, Michigan), depending upon the type of sample to be tested using the device. Compact absorbent pads are suitable for aqueous samples such as urine, and porous pads are preferred for viscous samples such as serum, plasma and blood. Essentially, the absorbent pad 18 retains the particulate or cellular fractions from the sample and allows the liquid portion to move towards the wicking material 15.

Absorbent end pad 26 preferably consists of materials that absorb and retain liquid and latex; this feature tends to restrict or prevent the reverse flow of latex, including colored latex. Without the end pad 26, the colored latex may begin to flow backwards approximately one hour after initiation of a test, and may appear in the "test complete" (port 10) and the "read result" (port 12) windows, resulting in a messy, uneven background. In addition, absorbent end pad 26 restricts or prevents the reverse flow of sample or sample components onto the wicking material.

Several absorbent pads were tested for their ability to prevent the reverse flow of colored latex in a reaction unit similar to reaction unit 2. The absorbent materials which appeared to be better than the control pad alone (Whatman D28, Whatman Manufacturing Inc., N.J. was used as the control pad) are as follows:

1. S&S 2727 (Schleicher and Schuell, W. Germany);
2. Multiform SG145 (Multiform Desiccants Inc., N.Y.);
3. Pall Ultipor GF Plus 1.0 μm (Pall BioSupport Corp., N.Y.) on top of Whatman D28. (The test materials were a thin layer; thus, they were layered on top of control pad D28 to have proper contact with the wicking material.);
4. Dri Mop Liquid Absorber (Multiform Desiccants Inc., N.Y.) on Whatman D28, or Dri Mop applied directly on the wicking material (15). (The test materials were powder gel; thus, they were sprinkled on top of control pad D28 to have proper contact with the wicking material.);
5. Ultra Pampers Plus Diapers (Proctor & Gamble, Ohio);
6. Gelok 3000, 4000, 5500 and 6000 A/F single/double ply laminate with #1080 polymer, Gelok 5000/Scrim 3A, Gelok 5011-HS, Gelok 6000 Airlay/single ply laminate with IM-1000 polymer (all from Gelok International Corp., Ohio), on top of Whatman D28. (As before, the test materials were a thin layer; thus, they were layered on top of control pad D28 to have proper contact with the wicking material.)

Although the invention has been described in the context of particular embodiments, it is intended that the scope of coverage of the patent not be limited to those particular embodiments, but be determined by reference to the following claims.

We claim:

1. A method of constructing a plurality of immunoassay devices having a common multi-purpose housing and a different finished appearance, comprising the steps of:

providing at least two identical housings each having an inside, an outside, and a top, said top having a plurality of apertures therein for providing access to the inside of said housing, wherein a first of said plurality of apertures is for receiving a sample;

inserting a web of wicking material in said at least two identical housings extending between second, third, and fourth of said plurality of apertures with said third aperture located between said second and fourth apertures, wherein said second, third, and fourth apertures provide access to said wicking material and said first aperture is in fluid communication with said wicking material;

applying reagents to said wicking material through at least said second and said third apertures, wherein the reagent applied to said wicking material through said third aperture becomes bound to said wicking material and the reagent applied to said wicking material through said second aperture is mobile when liquid is added to said first aperture, and reacts with an analyte in a sample and aid reagent applied to said wicking material through said third aperture to create a signal visible through said third aperture which is indicative of the assay result;

applying a first permanently affixed substantially coextensive web of opaque material having openings therein to the top of a first of said at least two identical housings such that only the first and third apertures are uncovered to form a first immunoassay device; and applying a second permanently affixed substantially coextensive web of opaque material having openings therein to the top of a second of said at least two identical housings such that the first and third apertures and at least one additional aperture are uncovered to form a second immunoassay device.

2. The method of claim 1, further comprising inserting an absorbent material inside said at least two identical housings wherein the absorbent material is in fluid flow contact with said wicking material and is located at said first aperture.

3. The method of claim 1, further comprising inserting an absorbent material inside said at least two identical housings wherein the absorbent material is in fluid flow contact with said wicking material and is located adjacent said fourth aperture.

4. The method of claim 1, wherein the at least two identical housings have a fifth aperture for receiving a desiccant, further comprising the steps of:

inserting the desiccant into said at least two identical housings through said fifth aperture prior to applying said web of opaque material; and covering said fifth aperture with said web of opaque material.

5. The method of claim 1, wherein the at least two identical housings have a fifth aperture forming a well for receiving a container.

6. A plurality of immunoassay devices having a common multi-purpose housing and a different finished appearance, comprising:

at least two identical housings each having an inside, an outside, and a top, said top having a plurality of apertures therein for providing access to the inside of said housing, wherein a first of said plurality of apertures is for receiving a sample;

a web of wicking material in said at least two identical housings extending between second, third, and fourth of said plurality of apertures with said third aperture located between said second and fourth apertures, wherein said second, third, and fourth apertures provide access to said wicking material and said first aperture is in fluid communication with said wicking material;

reagents applied to said wicking material at said second and said third apertures, wherein the reagent applied to said wicking material at said third aperture is bound to said wicking material and the reagent applied to said wicking material at said second aperture is mobile when liquid is added to said first aperture, and reacts with an analyte in a sample and said reagent at said third aperture to create a signal visible through said third aperture which is indicative of the assay result;

a first permanently affixed substantially coextensive web of opaque material having openings therein applied to the top of a first of said at least two identical housings such that only the first and third apertures are uncovered to form a first immunoassay device; and a second permanently affixed substantially coextensive web of opaque material having openings therein applied to the top of a second of said at least two identical housings such that the first and third apertures and at least one additional aperture are uncovered to form a second immunoassay device.

7. The devices of claim 6, further comprising an absorbent material inside said at least two identical housings wherein the absorbent material is in fluid flow contact with said wicking material and is located at said first aperture.

8. The devices of claim 6, further comprising an absorbent material inside said at least two identical housings wherein the absorbent material is in fluid flow contact with said wicking material and is located adjacent said fourth aperture.

9. The devices of claim 6, further comprising: a fifth aperture in the at least two identical housings and a desiccant inserted inside the at least two identical housings through the fifth aperture, wherein said fifth aperture is covered by said web of opaque material.

10. The devices of claim 6, wherein the at least two identical housings have a fifth aperture that is uncovered by said web of opaque material forming a well for receiving a container.

11. The devices of claim 6, wherein a reagent is applied to the wicking material at said fourth aperture said reagent producing a signal indicative of completion of the assay.

12. The devices of claim 6, wherein the web of opaque material comprises paper.

* * * * *